United States Patent [19]

Ogata et al.

[11] Patent Number: 5,700,789
[45] Date of Patent: Dec. 23, 1997

[54] ANTIALLERGIC COMPOSITION COMPRISING A PHOSPHORIC DIESTER COMPOUND

[75] Inventors: Kazumi Ogata, Toyonaka; Takahiro Sakaue, Itami; Shogo Sameshima, Moriguchi, all of Japan

[73] Assignee: Senju Pharmaceutical Co., Ltd., Osaka, Japan

[21] Appl. No.: 683,439

[22] Filed: Jul. 18, 1996

[30] Foreign Application Priority Data

Jul. 18, 1995 [JP] Japan .................................. 7-181156

[51] Int. Cl.$^6$ ................................. A61K 31/665
[52] U.S. Cl. ........................................ 514/100
[58] Field of Search .............................. 514/100

[56] References Cited

U.S. PATENT DOCUMENTS

| | | | |
|---|---|---|---|
| 4,564,686 | 1/1986 | Ogata ................................ | 549/220 |
| 4,888,329 | 12/1989 | Ogata et al. ........................ | 514/100 |
| 4,914,197 | 4/1990 | Yamamoto et al. ................. | 536/117 |
| 4,948,786 | 8/1990 | Shinamoto ......................... | 514/100 |
| 5,306,713 | 4/1994 | Suetsugu et al. .................. | 514/100 |

FOREIGN PATENT DOCUMENTS 0 127 471  12/1984  European Pat. Off. .
0 324 387   7/1989  European Pat. Off. .
430 045     6/1991  European Pat. Off. .

OTHER PUBLICATIONS

Britton et al., Am J. Respon. Crit. Care Med., vol. 151, 1 May 1995, pp. 1383–1387.

*Primary Examiner*—Jerome D. Goldberg
*Attorney, Agent, or Firm*—Wenderoth, Lind & Ponack

[57] ABSTRACT

This invention provides an antiallergic composition which comprises a phosphoric diester compound of the following formula or a pharmacologically acceptable salt thereof

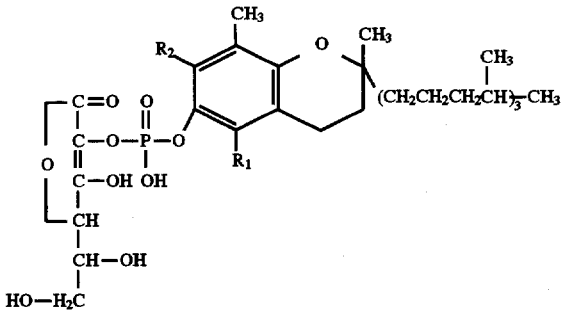

wherein $R_1$ and $R_2$ are the same or different and each represents hydrogen or methyl.

1 Claim, No Drawings

ANTIALLERGIC COMPOSITION COMPRISING A PHOSPHORIC DIESTER COMPOUND

BACKGROUND OF THE INVENTION

1. Field of the Invention

This invention relates to a useful antiallergic composition. More particularly, this invention relates to a useful antiallergic composition which comprises an ascorbyl tocopheryl phosphate compound or a pharmacologically acceptable salt thereof.

2. Description of the Prior Art

The compound for use in the antiallergic composition according to this invention is known as an anticataract drug, a prophylactic and therapeutic drug for climacteric disturbance, a skin-beautifying cosmetic (U.S. Pat. No. 4,564,686), an antioxidative agent (U.S. Pat. No. 5,306,713), an antiulcer drug (U.S. Pat. No. 4,888,329), an anti-inflammatory drug (U.S. Pat. No. 4,914,197), a prophylactic and therapeutic drug for ischemic disorder in organs (U.S. Pat. No. 4,948,786) and a Maillard reaction inhibitor (EP-A2-0430045), among a diversity of uses.

The inventors of this invention explored the pharmacological action profile of the ascorbyl tocopheryl phosphate compound and discovered that they are also useful as an antiallergic drug. The present invention was accomplished based on this new finding.

SUMMARY OF THE INVENTION

This invention provides a useful antiallergic composition which comprises a phosphoric diester compound or a pharmacologically acceptable salt thereof.

This invention, therefore, is directed to an antiallergic composition which comprises a phosphoric diester compound of the following formula or a pharmacologically acceptable salt thereof (hereinafter referred to as the compound)

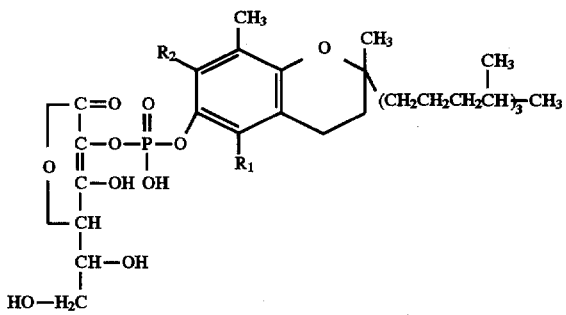

wherein $R_1$ and $R_2$ are the same or different and each represents hydrogen or methyl.

DETAILED DESCRIPTION OF THE INVENTION

The present compounds are already known to have the various pharmacological activities as mentioned above. However, it is not yet known that the compounds have antiallergic activity.

The compound for use in the antiallergic composition according to this invention can be synthesized by the processes described in U.S. Pat. Nos. 4,564,686 or 4,914,197, among others.

The compound for use in the antiallergic composition according to this invention may be a free compound or a pharmacologically acceptable salt thereof. The pharmacologically acceptable salt typically includes salts with alkali metals such as sodium, potassium, etc. and salts with alkaline earth metals such as calcium, magnesium, and so forth. However, any other salts can likewise be employed only if it is pharmacologically acceptable.

The antiallergic composition according to this invention may contain one or more species of the present compound according to the intended use and need.

The compound as the active ingredient of the antiallergic composition according to this invention is a safe compound with only a very low toxic potential and can, therefore, be used for accomplishing the above-mentioned object of this invention [$LD_{50}$ of L-ascorbyl DL-α-tocopheryl phosphate potassium (hereinafter referred to briefly as EPC-K) is 5 g/kg p.o. (rats), $\geq 100$ mg/kg i.v. (rats)].

The allergic disease that can be treated with the antiallergic composition of the present invention includes but is not limited to bronchial asthma, pollinosis, allergic rhinitis, alimentary allergic gastritis, allergic diarrhea, ulcerative colitis, stomatitis, nodular periarteritis, obliterating endarteritis, endocarditis, urticaria, edema, contact dermatitis, phlyctenule, sympathetic ophthalmia, allergic conjunctivitis, and allergic keratitis.

The antiallergic composition of this invention can be administered either orally or parenterally. The dosage form in which the antiallergic composition of this invention can be provided includes solid preparations such as tablets, granules, powders, capsules, etc. and liquid preparations such as injections, syrups, eye-drops, nose-drops, all of which can be manufactured by the established pharmaceutical procedures. These dosage forms may contain a variety of additives which are commonly employed, such as excipients, binders, disintegrators, dispersing agents, reabsorption promoters, buffers, surfactants, solubilizer, preservatives, emulsifiers, isotonizing agents, stabilizers, pH control agents, and so forth.

The dosage of the present compound for use as an antiallergic drug is dependent on species of the compound, the disease to be treated, the patient's age and body weight, clinical manifestations that must be controlled and dosage form, etc. but taking an injection as an example, about 1 mg to about 100 mg per adult man can be administered once a day and in the case of an oral preparation, about 10 mg to about 1,000 mg per adult man can be administered a few times a day. As a topical ophthalmic dosage form, a few drops of a solution or suspension of about 0.01 (w/v) % to 0.5 (w/v) % concentration can be advantageously instilled in the eye several times a day. In the case of an ointment, about 1 (w/w) % to 10 (w/w) % can be incorporated into the composition.

Unless contrary to the spirit and object of this invention, the antiallergic composition of this invention may further contain one or more other antiallergic drugs and/or other kinds of pharmacologically active ingredients.

EXAMPLES

The following examples and formulation examples are further illustrative of this invention.

Example 1

Effect of the Compound of the Invention on Palpebral Edema

The effect of the compound of the invention on the palpebral edema induced by the histamine releaser Compound 48/80 (the condensation product of N-methyl-p-methoxy-phenethylamine with formaldehyde) (Sigma Chemical Company) was evaluated.

Test Materials (1) 0.1% L-ascorbyl DL-α-tocopheryl phosphate sodium (Abbreviation: EPC-Na) (dissolved in physiological saline and adjusted to pH 7.0)

(2) 0.1% diphenhydramine hydrochloride (an antihistaminic) (dissolved in physiological saline)

Method: Male SD rats weighing about 180 g were used.

The rats were divided into three groups, i.e. a control group, an EPC-Na group, and a diphenhydramine HCl group, and 20 μl/eye of 0.008% Compound 48/80 (dissolved in physiological saline) was injected subconjunctivally at both lids to induce palpebral edema. Two (2), 1, and 0.5 hr before subconjunctival injection and 0.5, 1.5, and 2.5 hr after the injection, rats in the control group were topically treated with 5 μl/eye of physiological saline and those in the EPC-Na group and diphenhydramine HCl group were similarly treated with 5 μl/eye of the corresponding test materials. Four (4) hr after injection of Compound 48/80 (1.5 hr after the last instillation), the rats were sacrificed and the edematous portion of the palpebra was excised, its wet weight (mg) was determined, and the edema inhibition rate (%) with respect to the control group was calculated.

Results

The results are shown in Table 1.

TABLE 1

Effect of the compound of the invention on palpebral edema

| Group | Edema weight (mg) | Inhibition rate (%) |
|---|---|---|
| Control group | 114.4 ± 11.6 | — |
| EPC-Na group | 76.1 ± 11.6* | 33.5 |
| Diphenhydramine HCl group | 63.2 ± 8.2* | 44.8 |

*Significantly different from the control group at $p<0.001$

It is apparent from Table 1 that compared with the control group, the EPC-Na group showed an edema inhibition rate of 33.5%. This result indicates the usefulness of the compound of the invention as an antiallergic drug.

Example 2

Effect of the Compound of the Invention on Type III Allergic Conjunctivitis

The effect of the compound of the invention on Type III allergic conjunctivitis was evaluated.

Test Materials (1) 0.1% EPC-Na (dissolved in physiological saline)

(2) 0.15% dexamethasone sodium metasulfobenzoate (Visualin Ophthalmic Solution (registered trademark, Senju Pharmaceutical Co. Ltd.) (0.1% as dexamethasone, hereinafter referred to briefly as dexamethasone)

Method

The rats were divided into three groups, namely a control group, an EPC-Na group and a dexamethasone group, and 30 μl of rat antirabbit serum was injected subconjunctivally at both lids. Two (2), 1.5, and 0.5 hr before subconjunctival injection and 0.5, 1.5, and 2.5 hr after the injection, rats in the control group were topically treated with 5 μl/eye of physiological saline and those in the test groups were similarly treated with 5 μl/eye of the respective test materials. At 0.5 hr after the last instillation, the rats were sacrificed, the edema weight (wet weight/mg) was determined, and the inhibition rate (%) with respect to the control group was calculated.

Results

The results are shown in table 2.

TABLE 2

Effect of the compound of the invention on Type III allergic conjunctivitis

| Group | Edema weight (mg) | Inhibition rate (%) |
|---|---|---|
| Control group | 84.8 ± 6.9 | — |
| EPC-Na group | 57.4 ± 8.1* | 32.3 |
| Dexamethasone group | 58.2 ± 3.8* | 31.3 |

Each value is the mean ± S.D. (n = 4)

Significantly different from the control group at $p<0.001$

It is apparent from Table 2 that compared with the control group, both the EPC-Na group and the dexamethasone group showed significant edema inhibitions amounting to about 30%. The above results indicate the usefulness of the compound of the invention as an antiallergic drug.

Formulation Example 1
Oral Tablet

| EPC-K | 100 mg |
|---|---|
| Lactose | 75 mg |
| Starch | 20 mg |
| Polyethyleneglycol 6000 | 5 mg |

The above ingredients per tablet are mixed in the conventional manner to provide a tablet. Where necessary, the tablet may be sugar-coated.

Formulation Example 2
Injection

| EPC-K | 200 mg |
|---|---|
| Mannitol | 5.0 g |
| 1N-Sodium hydroxide | q.s. |
| Distilled water | To make 100 ml pH 6.5 |

The above ingredients are mixed and filtered through a bacterial filter in the routine manner. The filtrate is aseptically distributed in glass ampules, 5 ml per ampule, to provide an injection.

Formulation Example 3
Eye-drops

| EPC-Na | 0.1 g |
|---|---|
| Boric acid | 1.5 g |
| Borax | 0.3 g |
| Methyl p-hydroxybenzoate | 0.026 g |
| Propyl p-hydroxybenzoate | 0.014 g |
| Sterilized purified water | To make 100 ml |

The above ingredients are mixed in the conventional manner to provide an eye-drops.

Formulation Example 4
Ointment

| EPC-Na | 5.0 g |
|---|---|
| Glycerin | 12.0 g |
| Stearyl alcohol | 25.0 g |
| White petrolatum | 25.0 g |
| Methyl p-hydroxybenzoate | 0.025 g |
| Propyl p-hydroxybenzoate | 0.015 g |
| Sterilized purified water | To make 100 g |

The above ingredients are mixed in the conventional manner to provide an ointment.

Formulation Example 5

Gel

| EPC-K | 0.5 g |
|---|---|
| Carboxyvinylpolymer | 1.0 g |
| Triethanolamine | q.s. |
| Propyl p-hydroxybenzoate | 0.014 g |
| Ethanol | 30 ml |
| Sterilized purified water | To make 100 ml |
| | pH 7.0 |

The above ingredients are mixed in the conventional manner to provide a gel.

Formulation Example 6

Syrup

| EPC-Na | 2.0 g |
|---|---|
| 70% aqueous solution of D-sorbitol | 70 ml |
| Methyl p-hydroxybenzoate | 0.028 g |
| Propyl p-hydroxybenzoate | 0.012 g |
| Sterilized purified water | To make 100 ml |
| | pH 6.0 |

The above ingredients are mixed in the conventional manner to provide a syrup.

What is claimed is:

1. A method for the treatment of allergic disease which comprises administering to a patient in need thereof an effective amount of a compound of the following formula or a pharmacologically acceptable salt thereof

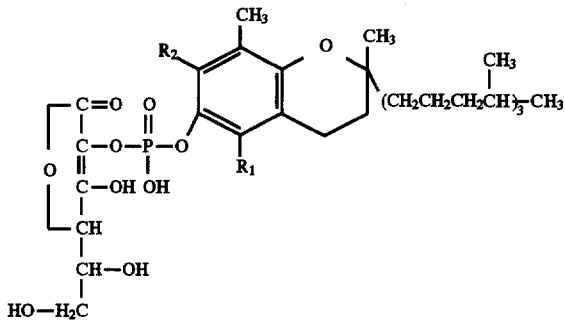

wherein $R_1$ and $R_2$ are the same or different and each represents hydrogen or methyl.

* * * * *